United States Patent
Elsley

(10) Patent No.: US 7,125,897 B1
(45) Date of Patent: Oct. 24, 2006

(54) COMBINED THERAPIES FOR ATHEROSCLEROSIS TREATMENT

(75) Inventor: David Elsley, Oakville (CA)

(73) Assignee: Vasogen Ireland Limited(IE)

( * ) Notice: Subject to any disclaimer, the term of this patent is extended or adjusted under 35 U.S.C. 154(b) by 536 days.

(21) Appl. No.: 10/089,362

(22) PCT Filed: Sep. 25, 2000

(86) PCT No.: PCT/CA00/01112

§ 371 (c)(1),
(2), (4) Date: Jan. 14, 2003

(87) PCT Pub. No.: WO01/22976

PCT Pub. Date: Apr. 5, 2001

(30) Foreign Application Priority Data

Sep. 24, 1999 (CA) .................. 2283374
Sep. 28, 1999 (CA) .................. 2283975

(51) Int. Cl.
*A61K 31/44* (2006.01)
*A61K 31/40* (2006.01)
*A61K 31/35* (2006.01)
*A61K 31/225* (2006.01)
*A01N 63/00* (2006.01)

(52) U.S. Cl. .................. 514/345; 514/419; 514/423; 514/460; 514/547; 424/93.73; 604/4.01; 604/6.08

(58) Field of Classification Search ................ 514/345, 514/419, 423, 460, 547; 424/93.73; 604/4.01, 604/6.08
See application file for complete search history.

(56) References Cited

U.S. PATENT DOCUMENTS

| 5,426,116 | A | * | 6/1995 | Bisaccia et al. ............. 514/455 |
| 5,705,518 | A | * | 1/1998 | Richter et al. .............. 514/410 |
| 5,980,954 | A | * | 11/1999 | Bolton ....................... 424/613 |
| 6,264,646 | B1 | * | 7/2001 | Stewart ....................... 604/522 |
| 6,432,399 | B1 | * | 8/2002 | Tremblay et al. ........... 424/93.7 |
| 2003/0157114 | A1 | * | 8/2003 | Bolton .................... 424/184.1 |

FOREIGN PATENT DOCUMENTS

| CA | 2296723 | 3/1999 |
| WO | 96/34613 | 11/1996 |
| WO | 98/07436 | 2/1998 |
| WO | 99/11260 | 3/1999 |
| WO | 99/13890 | 3/1999 |
| WO | 00/29003 | 5/2000 |

OTHER PUBLICATIONS

The Merck Manual of Diagnosis and Therapy, Berkow et al. (eds.), published 1982 by Merck & Co., Inc. (NJ), pp. 386-389 and 550-555.*
Alegret, M., et al. "Effect of hypolipidemic drugs on key enzyme activities related to lipid metabolism in normolipidemic rabbits." *E. J. Pharmacol.* 347: 283-291 (1998).
Bandoh, T., et al. "Fluvastatin Suppresses Atherosclerotic Progression, Mediated Through Its Inhibitory Effect on Endothelial Dysfunction, Lipid Peroxidation, and Macrophage Deposition." *J. Cardio. Pharmacol.* 35: 134-144 (2000).
Bocan, T.M.A., et al. "Antiatherosclerotic activity of inhibitors of 3-hydroxy-3-methylglytaryl coenzyme A reductase in cholesterol-fed rabbits: a biochemical and morphological evaluation." *Atherosclerosis.* 111: 127-142 (1994).
Dowell, F.J., et al. "Development and Progression of Atherosclerosis in Aorta From Heterozygous and Homozygous WHHL Rabbits." *Arteriosclerosis, Thrombosis, and Vascular Biology.* 15(8): 1152-1160 (1995).
Gambhir, D.S. "Statin Therapy for Prevention of Coronary Artery Disease with Average Cholesterol Levels." *Indian Heart J.* 51: 19-21 (1999).
Farnier, M., et al. "Current and Future Treatment of Hyperlipidemia: The Role of Statins." *Am. J. Cardiol.* 82(48): 3J-10J (1998).
Kroon, A.A., et al. "The effect of cholesterol reduction on the endothelial function and progression of atherosclerosis in WHHL rabbits." *Atherosclerosis.* 103(221-230 (1993).
LaRosa, J.C. "Future Cardiovascular End Point Studies: Where Will the Research Take Us?" *Am. J. Cardiol.* 84: 454-458 (1999).
Pederssen, T.R. "Statin trials and goals of cholesterol-lowering therapy after AMI." *Am. Heart J.* 138: S177-S182 (1999).
Reynolds, J.E.F. "Martindale, the Extra Pharmacopeia, Thirty-second Edition." London, Royal Pharmaceutical Society. p. 1268-1279. (1994).
Ross, S.D., et al. "Clinical Outcomes in Statin Treatment Trials." *Arch. Intern. Med.* 159: 1973-1802 (1999).
Vaughan, C.J., et al. "Neuroprotective Properties of Statins in Cerebral Ischemia and Stroke." *Stroke.* 30: 1969-1973 (1999).

(Continued)

Primary Examiner—Raymond J. Henley, III
(74) Attorney, Agent, or Firm—Foley & Lardner LLP

(57) ABSTRACT

There is provided a combination treatment for slowing or arresting the progression and/or effecting the regression of atherosclerotic plaque deposits in a mammalian patient, said combination treatment including the administration to the patient of a cholesterol lowering drug such as a statin, and the administration to the patient of an aliquot of a patient's own blood which has been treated ex vivo with one or more stressors selected from an oxidative environment, thermal stress and UV light.

22 Claims, No Drawings

OTHER PUBLICATIONS

Wheeler, D.C. "Are There Potential Non-Lipid-Lowering Uses of Statins?" *Drugs.* 5(6): 517-522 (1998).

Bernini, F., et al. (2001). "Safety of HMG-CoA Reductase Inhibitors: Focus on Atorvastatin," *Cardiovascular Drugs and Therapy*, 15:211-218.

Blum, C. (1994). "Comparison of Properties of Four Inhibitors of 3-Hydroxy-3-Methylglutaryl-Coenzyme A Reductase," *Am. J. Cardio,* 73:3D-11D.

"Compendium of Pharmaceuticals and Specialities, 35th Edition, 2001: The Candian Reference for Health Professionals," Candaian Pharmacists Association, 815-818, 834-836, 921-923, 1236-1239, 1776-1778.

Hsu, I., et al. (1995). "Comparative Evaluation of the Safety and Efficacy of HMG-CoA Reductase Inhibitor Monotherapy in the Treatment of Primary Hypercholesterolemia," *Ann. Of Pharmac.*, 29:743-759.

Malhotra, H., et al. (2001). "Atorvastatin: An Updated Review of its Pharmacological Properties and Use in Dyslipidaemia," *Adis Drug Evaluation Drugs*, 61(12):1835-1881.

Newman, C., et al. (2003). "Safety of Atorvastatin Derived from Analysis of 44 Completed Trials in 9,416 Patients," *Am. J. Cardio.,* 92:670-676.

"Lescol," *Physician's Desk Reference,* http://www.pdrhealth.com/drug_info/rxdrugprofiles/drugs/les1221.shtml (Feb. 12, 2004).

"Lipitor," *Physician's Desk Reference,* http://www.pdrhealth.com/drug_info/rxdrugprofiles/drugs/lip1230.shtml (Feb. 12, 2004).

"Mevacor," *Physician's Desk Reference,* http://www.pdrhealth.com/drug_info/rxdrugprofiles/drugs/mev1260.shtml (Feb. 12, 2004).

"Pravachol," *Physician's Desk Reference,* http://www.pdrhealth.com/drug_info/rxdrugprofiles/drugs/pra1344.shtml (Feb. 12, 2004).

"Zocor," *Physician's Desk Reference,* http://www.pdrhealth.com/drug_info/rxdrugprofiles/drugs/zoc1500.shtml (Feb. 12, 2004).

Athyros et al. "Safety and Efficacy of Long-term Statin-Fibrate Combinations in Patients with Refractory Familial Combined Hyperlipidemia" *Am. J. Cardiol.* 80:608-613 (1997).

Tikkanen, Matti J. "Statins: within-group comparisons, statin escape and combination therapy" *Current Opinion in Lipidology* 7:385-388 (1996).

Orekhov et al. "Antiatherosclerotic and antiatherogeni effects of a calcium antagonist plus statin combination: amlodipine and lovastatin" *Int. J. Cardiol.* (Suppl. 2):S67-S77 (1997).

Kostner, K.M. "Aggressive Therapie and Kombinationstherapie bie schweren Hyperlipidämien" WMW- May 6, 1999 Themenheft: "HMG-CoA-Reduktase-Hemmer" 1-3.

Feher et al. "Long-term safety of statin-fibrate combination treatment in the management of hypercholesterolaemia in patients with coronary artery disease" *Br. Heart J.* 74:14-17 (1995).

Orekhov et al. "Anti-Atherogenic Effect of Calcium Antagonist Plus Statin Combination," *Cardiovascular Drugs and Therapy, Kluwer academic Publishers*, Boston, U.S. vol. 11, No. 2:350 (1997).

* cited by examiner

COMBINED THERAPIES FOR ATHEROSCLEROSIS TREATMENT

FIELD OF THE INVENTION

This invention relates to compositions and procedures for treatment of elevated lipid levels in the serum of mammalian patients, and for treatment of atherosclerosis and cardiovascular disorders associated therewith or resulting therefrom.

BACKGROUND OF THE INVENTION

Hyperlipidemias such as hypercholesterolemia and elevated serum triglyceride levels are among the most potent risk factors in the causation of atherosclerosis, which is the build-up of fatty plaque deposits within the walls of blood vessels. For example, high levels of serum cholesterol bound to low density lipoprotein (LDL), intermediate density lipoprotein (IDL) or very low density lipoprotein (VLDL) are known to correlate strongly with the occurrence of atherosclerosis in humans. In particular, it is known that the higher the circulating levels of cholesterol in the form of LDL, IDL and VLDL cholesterol, and the higher the circulating levels of other lipids such as triglycerides, the more likely it is that cholesterol and lipids will be deposited within the blood vessel wall and cause or contribute to atherosclerosis.

In hypercholesterolemia, for example, the increase in the blood cholesterol level is associated mainly with a rise in the concentration of LDL, IDL and VLDL cholesterol. However, the specific causes of hypercholesterolemia are complicated and varied. At least one kind of hypercholesterolemia, known as familial hypercholesterolemia, is caused by a mutation in the gene for the LDL receptor that moves cholesterol out of the blood, primarily in the liver. Much more commonly, hypercholesterolemia has been associated with genetic factors and high dietary intake of saturated fatty acids and cholesterol, resulting in elevated blood cholesterol levels. High serum triglyceride levels have also been associated with high dietary intake of fatty acids.

Reduction of hyperlipidemia, including hypercholesterolemia, results in a delayed onset of atherosclerosis and a decrease in the progression of atherosclerosis, thus reducing the risk of coronary heart disease. Atherosclerosis, the major cause of most cardiovascular disorders, is a complex process involving the blood vessel wall, many different blood elements and the immune system. Recent evidence indicates that immune-related inflammation of the Th1 type is a major factor in the initiation, progression and manifestations of the disease. Down-regulation of the Th1 type immune response has been shown experimentally to prevent the development of, and/or cause regression of, atherosclerosis.

Some forms of hyperlipidemia, including hypercholesterolemia, are potentially partially reversible with current techniques of preventive management. Taking cholesterol-lowering drugs can result in a reduction in serum cholesterol, and other drugs may lower serum triglyceride levels. Dietary therapy is usually recommended for all patients with hyperlipidemia but the effect is often not sufficient to reduce risk optimally.

BRIEF REFERENCE TO THE PRIOR ART

A wide variety of cholesterol-lowering drugs are available on the prescription drug market, and are widely prescribed. These include the so-called "statin" drugs (lovastatin, simvastatin, pravastatin, fluvastatin, atorvastatin and cerivastatin), which are generally known as HMG-CoA reductase inhibitors, since their mechanism of action is understood to be through the selective, competitive inhibition of the hepatic enzyme 3-hydroxy-3-methylglutaryl-co-enzyme A reductase. In some cases, e.g. simvastatin, the active molecule is a metabolite formed in the body after ingestion of the drug by the patient. In other cases, the administered drug (commonly a pharmaceutically acceptable salt) is itself the active molecule. Other classes of cholesterol-lowering drugs include the bile acid sequestrants (cholestyramine resin, colestipol hydrochloride); fibrates (bezafibrate, clofibrate, fenofibrate and gemfibrozil), niacin derivatives (niacin and xanthinol niacinate); and other miscellaneous compounds such as dextrothyroxine. All of these, but especially the statin drugs, have proved successful in reducing serum cholesterol levels in mammalian patients, so as to attack one of the underlying causes of the development of atherosclerosis.

Atherosclerosis, the build-up of fatty plaque deposits within the walls of blood vessels, commonly develops over a relatively lengthy period of time in patients. To-date, treatments such as diet adjustment and administration of cholesterol lowering drugs have slowed or even halted the development of atherosclerosis, but only limited success has been reported for causing regression of atherosclerosis, i.e. diminution of the atherosclerotic fatty plaque deposits. The need for procedures and compositions which will not only reduce serum lipid levels, especially cholesterol levels, in mammalian patients, but will also inhibit development and effect regression of atherosclerotic plaque deposits, is clearly apparent.

U.S. Pat. No. 4,681,893 describes the preparation and use of atorvastatin, and U.S. Pat. No. 5,273,995 Roth describes the preparation and use of atorvastatin calcium (marketed as Lipitor®), one of the leading cholesterol-lowering drugs. Similarly, U.S. Pat. No. 4,231,938 Monaghan et. al. describes lovastatin, its preparation and use; U.S. Pat. No. 4,444,784 Hoffmann et. al. describes simvastatin, its preparation and use; U.S. Pat. No. 4,346,227 Terehara et. al. describes pravastatin, its preparation and use; and U.S. Pat. No. 4,739,073 Kathawala describes fluvastatin, its preparation and use.

Hyperlipidemia is central to the development of atherosclerotic plaques, the growth of which impairs arterial blood flow. As noted above, all of the varous statin drugs act to lower plasma cholesterol effectively, by inhibiting hepatic hydroxymethyl glutaryl coenzyme A reductase, the enzyme that catalyzes the conversion of HMG-CoA to mevalonate, a precursor of steroids including cholesterol. Since cholesterol is an essential component of cell membranes and is required for cell proliferation, excessive lowering of serum cholesterol is undesirable. Accordingly, the amounts of statin drugs which can be safely administered is limited, for fear of development of side effects. Among the reported side effects of statin administration is elevation in hepatic enzyme levels, leading to hepatotoxicity. In addition, there are certain incompatibilities of statin drugs with other substances, which limits their use and their desirable dosage amounts. For example, concurrent therapy with erythromycin, cyclosporine, niacin and fibrates has been reported to increase the risk of myopathy in a significant proportion of patients receiving statins. None of the statins can properly be used during pregnancy, at least at their current effective dosage levels.

Moreover, there are significant differences between the respective statin drugs. Lovastatin, provastatin and simvastatin are pro-drugs, requiring conversion to the active hydroxy acid form in the body, whereas atorvastatin and cerivastatin are not pro-drugs, but are directly active. There are different circumstances and different patient conditions which indicate the choice of one of the statin drugs for administration, over the others.

U.S. Pat. No. 5,980,954 Bolton describes a process of treating an aliquot of a patient's blood extracorporeally, by simultaneous subjection to ozone/oxygen gaseous mixture, UV radiation and elevated temperature, and re-injection of the treated aliquot to the patient, for alleviation of a variety of autoimmune diseases including atherosclerosis (an autoimmune disease of the vasculature). Other patents and patent applications of Bolton and co-workers describe the application of similar treatments to alleviate and to precondition against various other medical disorders.

It is an object of the present invention to provide a treatment for atherosclerosis in which the benefits of statin treatment are enhanced, and/or in which the disadvantages associated with statin treatment for this purpose are reduced.

SUMMARY OF THE INVENTION

An aspect of the invention is the provision of a combination treatment for slowing or arresting the progression and/or effecting the regression of atherosclerotic plaque deposits in a mammalian patient, said combination treatment including the administration to the patient of a cholesterol lowering drug and the administration to the patient of an aliquot of a patient's own blood which has been treated ex vivo with one or more stressors selected from an oxidative environment, thermal stress and UV light.

Another aspect of the invention comprises the use of an aliquot of a patient's own blood which has been treated ex vivo with one or more stressors selected from an oxidative environment, thermal stress and UV light; and a cholesterol-lowering drug, for reducing serum lipid levels and/or combating development of atherosclerosis in a mammalian patient.

A further aspect is a process for enhancing the reduction of serum lipid levels in a mammalian patient caused by administration of a cholesterol-lowering drug, which comprises administering to the patient an aliquot of the patient's own blood which has been treated ex vivo with one or more stressors selected from an oxidative environment, thermal stress and UV light and administering to the patient a cholesterol-lowering drug.

DESCRIPTION OF THE PREFERRED EMBODIMENTS

The preferred cholesterol-lowering drugs for use in the present invention are the statin drugs referred to above, namely lovastatin, simvastatin, pravastatin, fluvastatin, atorvastatin and cerivastatin. However, other cholesterol-lowering drugs as mentioned above may also be used. To be effective in the present invention, they can be administered in dosages previously recommended and used when the drugs are administered alone, and by the same routes of administration. Such dosages and methods are well known to those killed in the art, and published in various pharmacoepias and drug compendiums, such as the current edition of the "Compendium of Pharmaceutical Speciaties," published by the Canadian Pharmaceutical Association. They can be administered over the same time periods over which the patient is undergoing administration of the modified blood aliquots, as described below. The administration of the cholesterol-lowering drug can precede the commencement of the patient's treatments with modified blood aliquots and can continue thereafter, if required. The modified blood treatments may precede the commencement of the administration of the statin drug, and conclude before its commencement. Modified blood treatment may alternate with cholesterol drug administration periods, overlap therewith or totally coincide therewith. A synergistic effect of the two treatments of the combination may be obtained in some circumstances.

The aliquot of blood used as a part of the combination therapy in the present invention is an aliquot of the patient's own blood which has been extracorporeally treated by being subjected to one or more stressors which have been found to modify the blood. The blood aliquot can be modified by subjecting the blood, or separated cellular or non-cellular fractions of the blood, or mixtures of the separated cells and/or non-cellular fractions of the blood, to stressors selected from thermal stress, ultraviolet light and oxidative environments such as treatment with ozone/oxygen mixtures, or any combination of such stressors, simultaneously or sequentially.

Effects of the treatment according to the present invention is a substantial reduction of lipid levels in serum and deposition of lipids within blood vessel walls, a retardation of the progression of plaque deposition, and in some cases to cause existing plaques to regress. It is believed that this observed vessel protection is due at least in part to the reduced serum lipid levels in subjects treated by the method of the present invention. However, the reduced deposition of lipids within blood vessel walls may also occur in the absence of a reduction in serum lipids. Synergistic interaction between the components of the combination therapy of the present invention may be observed in the rate or degree of serum lipid lowering, and/or in the rate or degree of atherosclerotic plaque deposition, and/or in the rate or degree of atherosclerotic plaque regression, and/or in the rate or degree of improvement in plaque stabilization. Anti-inflammatory action of the combined therapy, especially as derived from the treated blood ingredient of the combination, which is believed to have the effect of down-regulating the activity of the Th-1 component of the T-cells present in the blood, responsible for secretion of inflammatory cytokines such as IL-2, IFN-$\gamma$ and TNF-$\alpha$, and/or up-regulation of the Th-2 component of T-cells responsible for secretion of anti-inflammatory cytokines such as IL-10 or IL-4, is postulated to be at least part of an underlying mechanism of the success of the combination therapy in reducing atherosclerotic plaque.

The combination therapy of the invention can be administered not only to treat symptoms of atherosclerosis, but also as a preventative for patients at risk of development of atherosclerosis, and as a preventative in combating of cardiovascular disease.

The effect of the stressors is to modify the blood, and/or the cellular or non-cellular fractions thereof, contained in the aliquot. The modified aliquot is then re-introduced into the subject's body by any suitable method, preferably selected from intra-arterial injection, intramuscular injection, intravenous injection, subcutaneous injection, and intraperitoneal injection.

The preparation and use of such modified autologous blood aliquots in treatment of, inter alia, peripheral vascular disease has been previously disclosed in U.S. Pat. No. 5,591,457 Bolton. The disclosure of that patent is incorporated herein by reference, in its entirety.

The stressors to which the aliquot of blood is subjected ex vivo according to the method of the present invention are selected from temperature stress (blood temperature above or below body temperature), an oxidative environment and ultraviolet light, individually or in any combination, simultaneously or sequentially. Suitably, in human subjects, the aliquot has a volume sufficient that, when re-introduced into the subject's body and in the presence of the cholesterol-lowering drug in the body, a reduction in a serum lipid level and/or a retardation in progression or a regression of atherosclerotic plaque formation is achieved in the subject. Preferably, the volume of the aliquot is up to about 400 ml, preferably from about 0.1 to about 100 ml, more preferably from about 5 to about 15 ml, even more preferably from about 8 to about 12 ml, and most preferably about 10 ml.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and ultraviolet light, or ultraviolet light and oxidative stress. Care must be taken to utilize an appropriate level of the stressors to thereby effectively modify the blood to achieve an effect on the atherosclerotic condition.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, a lipid reduction and/or a retardation in progression or regression in the formation of atherosclerotic plaque will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about −5° C. to about 36.5° C., even more preferably from about 10° C. to about 30° C., and even more preferably from about 15° C. to about 25° C.

The oxidative environment stressor can be the application to the aliquot of solid, liquid or gaseous oxidizing agents. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the therapy is rendered ineffective. Suitably, the gas stream has an ozone content of up to about 300 µg/ml, preferably up to about 100 µg/ml, more preferably about 30 µg/ml, even more preferably up to about 20 µg/ml, particularly preferably from about 5 µg/ml to about 20 µg/ml, and most preferably about 14.5±1.0 µg/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.24±0.024 liters/min. The lower limit of the flow rate of the gas stream is preferably not lower than 0.01 liters/min, more preferably not lower than 0.1 liters/min, and even more preferably not lower than 0.2 liters/min.

The ultraviolet light stressor is suitably applied by irradiating the aliquot under treatment from a source of UV light while the aliquot is maintained at the aforementioned temperature and while the oxygen/ozone gaseous mixture is being bubbled through the aliquot. Preferred UV sources are UV lamps emitting UV-C band wavelengths, i.e. at wavelengths shorter than about 280 nm. Ultraviolet light corresponding to standard UV-A (wavelengths from about 315 to about 400 nm) and UV-B (wavelengths from about 280 to about 315) sources can also be used, either alone or in combination with each other and UV-C sources. For example, an appropriate dosage of such UV light, applied simultaneously with the aforementioned temperature and oxidative environment stressors, can be obtained from lamps arranged to surround the sample container holding the aliquot, operated at an intensity to deliver a total UV light energy at the surface of the blood of from about 0.025 to about 10 joules/cm$^2$, preferably from about 0.1 to about 3.0 joules/cm$^2$, may advantageously be used. Preferably, four such lamps are used.

The time for which the aliquot is subjected to the stressors is normally within the time range of up to about 60 minutes. The time depends to some extent upon the chosen intensity of the UV light, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting blood temperature, and the rate at which it can be warmed or cooled to a predetermined temperature, tends to vary from subject to subject. Such a treatment provides a modified blood aliquot which is ready for injection into the subject.

For use in the process of the present invention, the blood aliquot may be treated with the stressors using an apparatus of the type described in U.S. Pat. No. 4,968,483 to Mueller. The aliquot is placed in a suitable, sterile, UV light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

A patient preferably undergoes a course of treatments of removal of a blood aliquot, treatment thereof as described above and re-administration of the treated blood to the patient, with the cholesterol-lowering drug being administered as separate doses during this course of treatments. Such a course may be a daily treatment for 4–6 days, followed by an interval and then a second course of daily treatments for 4–6 day. A preferred dosage regimen for the treated blood portion of the combination therapy is the administration of from 2–4 aliquots of autologous blood treated with stressors extracorporeally as described above, with the administration of any pair of consecutive aliquots being either on consecutive days, or being separated by a rest period of from 1–21 days on which no aliquots are administered to the patient, the rest period separating one selected pair of consecutive aliquots being from about 3–15 days. A more specific, preferred dosage regimen would be a total of three treatments and aliquots, with the first and second aliquots being administered on consecutive days and a rest period of 11 days being provided, between the administration of the second and third aliquots. The combination therapy of the invention may be useful in treatment of hypercholestolemia resulting from all of the various aforementioned causes.

Statin drug administration may be at a lower than normal dosage during the treated blood administration course, or at the same level of dosage to obtain a faster plaque regression rate. The patient may have been taking the statin drug for a period of time before adopting the combination therapy of the invention, and may continue on the statin drug, at the same or at a reduced dosage level, following the termination of the combination therapy. The combination therapy, with further courses of blood aliquot removal, treatment and re-administration, may be repeated at intervals, of, say, 3–12 months, in the event that the effectiveness of the previous combination therapy wears off or that the continued administration of statin drug alone is insufficiently effective.

The combination therapy of the invention is believed to affect the endothelium in such a way that it is rendered more resistant to the passage and deposition of the aforementioned lipid fractions.

Suitable daily dosages of statin drugs for human patients in the combination therapy of the present invention are, as noted, generally in accordance with those previously used when statin drugs are administered alone. These are, in respect of atorvastatin, simvastatin, lovastatin, fluvastatin and pravastatin, from about 5 mg to about 200 mg daily, for an adult of normal body weight, preferably from about 10–80 mg. In respect of cerivastatin, an entirely synthetic compound, the most appropriate daily dosage is much lower, namely from about 0.1–0.8 mg. In the combination therapy of the invention, and afterwards, these dosages may be reduced. Oral administration of the statin drug, once per day, is most appropriate.

The benefits and advantages of the present invention may be demonstrated by proceeding in accordance with the following specific, non-limiting examples.

EXAMPLE 1

Animal Studies

Adult male New Zealand white rabbits are chosen as the test animals, since it is known that the effects of statin therapy in this species are reasonably predictive of the effects to be obtained in humans.

Four groups of animals are formed, on a random selection basis, of equal numbers (n=5–10). All are fed a high cholesterol diet, namely regular chow supplemented with 0.5% by weight of pure cholesterol. This feeding continues until a marked increase in the animals' serum cholesterol is noted, whereupon the treatment described below starts.

One group of animals (Group 1) is given no treatment, but is kept and monitored as control. A second group (Group 2) is administered a daily dose of simvastatin (2.5 mg/kg body weight) throughout the test period. A third group (Group 3) is given a course of stressed blood administrations. Each administration involves the intramuscular injection into the animal of a 1.5 ml portion of a 10 ml aliquot of blood previously extracted from the same animal by venipuncture, and submitted extracorporeally to oxidative stressing, while contained in a sterilized UV-transparent container with sodium citrate anticoagulant, by bubbling an oxygen/ozone mixture containing $14.5 \pm 1.0$ μg ozone/ml, with the remainder of the gas mixture comprising medical grade oxygen. The gas mixture is bubbled through the aliquot at a rate of $240 \pm 24$ ml/min, for a period of 3 minutes, with the aliquot being held at a steady temperature of $42.5° \pm 1.0°$ C., while UV radiation within the UV-C band, and including a wavelength of 253.7 nm is incident on the sample. An apparatus as described in U.S. Pat. No. 4,968,483 Mueller is used to prepare the stressed blood aliquot.

A fourth group of animals (Group 4) is given is given a course of stressed blood treatments as in the case of Group 3, but in addition receives a daily dose of simvastatin, as in the case of the Group 2 animals, over the entire period of the course of treatment.

A course of treatment involves three treatments, namely one injection on day 1, another injection on day 2, and a third injection on day 14.

Serum lipid levels are measured at intervals following the conclusion of the treatments. The levels are significantly lower in the animals of Group 4 than in those of any of the other groups.

After 6 weeks following the therapy, the animals are sacrificed, and plaque levels and endothelial function assessed. The animals of Group 4 have significantly reduced plaque levels and significantly enhanced endothelial function as compared with the other groups.

The improvements found in the Group 4 animals are indicative of a treatment of atherosclosis significantly improved over those of the other groups, and not simply explainable as an additive effect of the two therapies.

EXAMPLE 2

Clinical Trial

The efficacy and safety of the combination process of the present invention can be demonstrated with respect to improving endothelial function in patients with wide-spread atherosclerosis. For this purpose, a parallel group, double-blind, placebo controlled study is conducted in a statistically significant number (e.g. thirty) patients, with clinical evidence of both coronary artery disease and peripheral vascular disease. The primary assessment variable is the degree of dilation of the brachial artery following a period of total brachial artery occlusion. In the study, some patients receive the stressed blood treatment, as described below. Others receive the stressed blood treatment in combination with administration of a statin drug. Still others receive only the statin drug administration.

One of the hallmarks of atherosclerosis is the presence of systemic endothelial dysfunction, an abnormality which can be demonstrated in both involved and non-involved distributive arteries, and at the level of the resistance arterioles in the microcirculation. Endothelial dysfunction is probably the earliest event in the atherosclerotic process and can be demonstrated in the presence of most risk factors for atherosclerosis, including hyperlipidemia, diabetes mellitus, hypertension and smoking, even before there is histological evidence of atherosclerosis. Thus studies which show significantly improved endothelial function in patients with atherosclerosis, for example, with the use of lipid lowering drugs and anti-oxidants, have been interpreted as indirect evidence of improvement of atherosclerosis.

The most reliable non-invasive method of assessing systemic endothelial function, is by the measurement of the degree of dilation of the brachial artery, as measured by 2-D ultra sound, following a period of total limb ischemia. Changes in brachial artery dilation are accepted as surrogates for coronary artery endothelial function as well as being representative of systemic endothelial function. In brief, high-resolution ultrasound is used to measure brachial artery diameter during the vasodilator response induced by reactive hyperemia. A 5 minute occlusion of flow to the upper extremity produced by inflation of a blood pressure cuff, followed by release of the occlusion results in an immediate 5–10 fold increase in blood flow as a result of resistance vessel dilation (reactive hyperemia). This marked increase in flow and shear stress both serve as a stimulus for the release of nitric oxide with subsequent conduit vessel dilation (brachial artery). Dilation of conduit vessels in response to an increase in flow is mediated by endothelium-derived nitric oxide. In dogs where the endothelium has been removed, an increase in flow is incapable of causing dilation of the upstream conduit artery. Similar results are observed when nitric oxide is inhibited. In humans without atherosclerosis, an increase in flow induced by exercise, cold pressor testing, mental arithmetic or resistance vessel vasodilators results in a 15–20% dilation in the coronary conduit vessel. This response is attenuated in subjects with overt atherosclerosis. Flow-mediated coronary responses have been shown to parallel coronary vasomotor responses to acetylcholine. Taken together, these data convincingly demonstrate that flow-mediated vasodilation of the brachial artery is dependent on the endothelial release of nitric oxide.

The stressed blood treatment used in the study involves the collection of 10 ml of a patient's venous blood into 2-ml of sodium citrate 3.13% as anticoagulant. The blood sample is transferred to a sterile, disposable low-density polyethylene vessel (model #V7002) for ex vivo treatment and is then exposed to the following three stimuli:

1) An elevated temperature of 42.5° C.±1.0° C. at steady state controlled and monitored with a thermocouple;
2) a gas mixture of medical oxygen containing 14.5±1.0 ug/ml of ozone, at a flow rate of 240±24 ml/min for 3 minutes;
3) Ultra-violet light at a wavelength of 253.7 nm, and a total energy of 2.0 joules/cm$^2$.

The ex vivo treatment of the patient's blood sample is performed within a Blood Treatment Unit (model #V7001), generally described in U.S. Pat. No. 4,968,483 Mueller. The Unit regulates and monitors these physicochemical agents. The temperature of the blood is raised to 42.5° C., a process that takes up to 8 minutes depending upon the starting temperature of the blood sample. Before this temperature is reached the UV lights turn on, so that they reach maximum output by the time that the gas flow is initiated, which occurs when the temperature of the blood reaches 42.5° C. The total time of exposure to UV light is about 9 minutes. The gas mixture is bubbled through the blood sample at a flow rate of 240±24 ml/min for a period of 3 minutes while the temperature of the blood is maintained and UV irradiation continues. At the end of the treatment with the three stimuli (stressors), the blood is allowed to settle for 7 minutes. The device then signals that the treatment has been completed successfully. The entire process takes about 20 minutes.

Before injection of the patient's treated blood, 1 ml of 2% Novocain is injected intramuscularly into the gluteal muscle as a local anaesthetic.

Each patient receives stressed blood administration in combination with statin therapy, or stressed blood administration alone, or placebo, according to the following regimen:

initial injections on two consecutive days followed by one injection two weeks later. A second similar course of therapy is administered one month following completion of the first and then monthly for three months, with or without a daily dose of the chosen statin drug, at the recommended daily dose for the selected statin drug, throughout the entire period of the study, including the intervals between courses of stressed blood administration therapy. For adult patients of average body weight, these doses are:
Pravastatin—10, 20 or 40 mg
Lovastatin—20 mg
Simvastatin—5, 10, 20 or 40 mg
Fluvastatin—20 or 40 mg
Atorvastatin—20 mg
Cerivastatin—0.5 mg.

Brachial ultrasound studies are carried out pretreatment at baseline, one month following completion of the second course of therapy and one month following the final injection. Routine biochemistry, haematology, & urinalysis are performed at baseline and one month following the end of treatment to assess safety. Adverse events, if any, are recorded at each visit as well.

Patients are randomly assigned to treatment or placebo according to a computer-generated randomization code, and receive either stressed blood administration in combination with statin drug treatment, or stressed blood administration alone, or placebo (normal saline) according to the lowest (or next available) number in the randomization sequence. Treatment is assigned in ascending chronological order.

All physicians and research nurses in charge of patient assessment and data entry remain blinded throughout the study. For patient blinding, both the treatment group and the placebo group patients have similar 10 ml of blood samples drawn on each treatment day. The placebo group receives 10 ml of normal saline (warmed to 37° C.) together with 1.0-ml local anesthetic instead of 10 ml of their treated blood. The placebo group is randomized prospectively and receives placebo injections according to the same schedule as the treated group. A separate, unblinded nurse, under a procedure which ensures maintenance of patient blinding, carries out the venipuncture, subsequent handling of blood samples, and administration of the placebo or the stressed blood to patients.

On each visit, either 10 ml of the patient's treated blood sample or 10 ml saline is injected intramuscularly into the same patient's gluteal muscle, together with a local anaesthetic (1 ml of 2% Novocain or equivalent) at the injection site. To avoid intravenous injection, the plunger of the syringe containing the clear and colourless local anaesthetic is pulled back and observed for blood. Once the anaesthetic is injected, the needle remains in situ and the syringe is replaced with the syringe containing either the treated blood sample or the saline.

To minimise the possibility of administering the wrong blood to a patient, the two syringes and the disposable blood container used for an individual patient's treatment are labelled with the same unique serialised number, and the same number is affixed to the patient, at the time of venepuncture. Before blood is loaded into the disposable blood container, the number on the syringe containing the patient's blood is matched to the number on the container. After blood treatment, the number on the syringe used to remove blood from the disposable blood container is matched to that on the container. Before re-injecting the treated blood, the number on the syringe is matched with the number on the patient. The operator is required to complete a Patient Matching Certificate recording all number matches to ensure that this is accomplished.

Patients receive treatment over a period of five months.

The patient study number, date, time, and status of treatment, blood treatment number, statin drug identity and dosage where applicable and treatment count is recorded at each treatment visit. In addition, details of the process itself, including temperature, oxygen flow-rate, ozone concentration, UV exposure time and intensity and bubbling action are recorded at 30 second intervals throughout the process If oxygen-flow rate, ozone concentration or temperature fall outside the process specification, the process aborts.

Blinding is broken if there is an adverse event possibly requiring discontinuation of either the local anesthetic or the stressed blood administration therapy. The investigator is provided with a sealed code break, which enables breaking the blinding code for an individual patient. This only occurs in the event of a medical emergency, which requires immediate identification of the study treatment. The investigator is authorized to break the code for the patient only.

Suitable patients for use in this study, i.e. inclusion criteria, are those who have evidence of existing coronary artery disease through any one of:
 angiography
 previous verified MI
 previous CABG or angioplasty
 Angina pectoris due to proven epicardial CAD
 Co-existing evidence of obstructive Peripheral Vascular Disease (PVD) through any one of:
 angiography
 previous bypass graft(s) or angioplasty
 intermittent claudication with Ankle/Brachial pressure index (ABPI)<0.8.

The patients may be male or female, 18–80 years of age. Females included in the study must be post-menopausal, surgically sterilised or of childbearing potential who do not plan to become pregnant during the course of the study and are using an acceptable method of contraception as determined by the investigator. Females of childbearing potential must have a negative pregnancy test prior to entry to the treatment phase of the study and the pregnancy test is repeated at the end of study visit.

Patients excluded from the study are any who are unable to undergo brachial ultrasound testing, or those patients who initiated or needed adjustment of the following medications during the 8 weeks prior to randomization:
 Beta blockers;
 Calcium channel blockers
 Lipid-lowering therapy;
 ACE Inhibitors;
 Dipyridamole;
 Omega-3 Fatty Acids;
 L-Arginine Supplements;
 Losartan
 Antihypertensive therapy;
 Antioxidants (including vitamin E);
 Aspirin;
 Pentoxifylline;
 Peripheral vascular or cardiac phoshodiesterase inhibitors
 Any other vasoactive medications.

Patients should, of course, otherwise be of generally good health and not at recognizable risk to the proposed treatments.

Brachial ultrasound studies are carried out at the beginning and at the final visit one month after the final stressed blood administration treatment.

EXAMPLE 3

Preliminary Studies on Human Patients

A 59 yr. old white female with intermittent claudication (a cramping pain caused by arterial obstruction and indicative of the presence of a relatively advanced stage of atherosclerosis) in her left leg, was administered fluvastatin 20 mg. daily for hypercholesterolemia. Her initial ankle/brachial artery pressure ratio (ABPI) in the left leg was 0.60, normal values being greater than 0.9. After 9 treatments with intramuscular administration of a 10 ml aliquot of her own blood stresses as described in Example 2, over 3 weeks, her ABPI had increased to 0.66, and 2 months after the end of treatment schedule was 0.75. Accepted margin of error for this test is 0.1 The increase in the ABPI is indicative of a decrease in the degree of major vessel obstruction by atherosclerotic plaque. This indicates a significant, probably synergistic, effect of the stressed blood administration and the statin causing more rapid regression of the plaque. The cholesterol level of the patient was reported to be moderately high.

In a separate investigation, a female patient 59 years of age suffering from peripheral arterial occlusive disease (a consequence of atherosclerosis) and receiving a regular, normal daily dose of lovastatin received 10 treatments of autologous stressed blood prepared as described above (10 ml aliquots, administered intramuscularly) over a 14-week period. As a result, her posterior tibial/brachial pressure index increased from 0.69 to 0.85, a very significant change. Her dorsalis (foot artery)/brachial pressure index also increased, from 0.77 to 0.85. Further, her claudication distance (walking distance before experiencing cramping pain in the legs) was also improved, all indication of an alleviation of atherosclerosis.

What is claimed is:

1. In a method for treating atherosclerosis in a mammalian patient with a statin drug wherein the improvement comprises administering to the patient an aliquot of the patient's blood that has been treated ex vivo with one or more stressors, selected from the group consisting of oxidative stress, thermal stress, and UV light.

2. The method of claim 1 wherein the static drug is selected from the group consisting of atorvastatin, pravastatin, lovastatin, fluvastatin, simvastatin, and cerivastatin.

3. The method of claim 1 wherein the aliquot of the patient's blood has a volume of from 0.1 to 100 ml.

4. The method of claim 1 wherein the blood aliquot has been treated ex vivo with oxidative stress and UV light, and optionally with thermal stress.

5. The method of claim 4 wherein the oxidative stress is a chemical oxidizing agent, said chemical oxidizing agent being applied to the blood aliquot while the blood aliquot is subjected to UV light.

6. The method of claim 5 wherein the chemical oxidizing agent is a gaseous mixture of ozone and oxygen, said gaseous mixture being applied by bubbling through the blood aliquot while the blood aliquot is subjected to UV light.

7. The method of claim 6, wherein a thermal stressor, in the form of a temperature above or below normal body temperature, is applied to the blood aliquot simultaneously with the gas mixture and the UV light.

8. The method of claim 1 wherein the UV light stressor is UV light in the UV-C band wavelength.

9. The method of claim 1 wherein the stressors are applied ex vivo to the blood aliquot for a period of from 2 to 5 minutes.

10. The method of claim 2 wherein the statin drug is atorvastatin administered at a daily dosage of from 5 to 200 mg.

11. The method of claim 2 wherein the statin drug is pravastatin administered at a daily dosage of from 5 to 200 mg.

12. The method of claim 2 wherein the statin drug is simvastatin administered at a daily dosage of from 5 to 200 mg.

13. The method of claim 2 wherein the statin drug is fluvastatin administered at a daily dosage of from 5 to 200 mg.

14. The method of claim 2 wherein the statin drug is lovastatin administered at a daily dosage of from 5 to 200 mg.

15. The method of claim 2 wherein the statin drug is cerivastatin administered at a daily dosage of from 0.1 to 0.8 mg.

16. The method of claim 1 wherein administration of the statin occurs prior to administration of the blood that has been treated ex vivo with one or more stressors.

17. The method of claim 1 wherein administration of the statin drug occurs simultaneously with administration of the blood that has been treated ex vivo with one or more stressors.

18. The method of claim 1 wherein administration of the statin drug overlaps administration of the blood that has been treated ex vivo with one or more stressors.

19. The method of claim 1 wherein administration of the blood that has been treated ex vivo with one or more stressors occurs prior to administration of the statin drug.

20. A method of slowing or arresting the progression and/or effecting the regression of atherosclerotic plaque deposits and/or improving the stability of such plaques in a mammalian patient, the method comprising administering to the patient a statin drug and an aliquot of the patient's own blood which has been treated ex vivo with one or more stressors, selected from the group consisting of an oxidative stress, thermal stress, and UV light.

21. A method of reducing serum lipid levels and/or combating the development of atherosclerosis in a mammalian patient, the method comprising:
   a) administering to the patient an aliquot of the patients own blood which has been treated ex vivo with one or more stressors, selected from the group consisting of, an oxidative stress, thermal stress, and UV light; and
   b) administering to the patient a statin drug.

22. A method of enhancing the reduction in serum lipid levels in a mammalian patient caused by administration of a statin drug, the method comprising:
   a) administering to the patient an aliquot of the patient's own blood which has been treated ex vivo with one or more stressors, selected from the group consisting of an oxidative stress, thermal stress, and UV light; and
   b) administering to the patient a statin drug.

* * * * *

UNITED STATES PATENT AND TRADEMARK OFFICE
CERTIFICATE OF CORRECTION

PATENT NO.         : 7,125,897 B1                                    Page 1 of 1
APPLICATION NO. : 10/089362
DATED              : October 24, 2006
INVENTOR(S)        : David Elsley It is certified that error appears in the above-identified patent and that said Letters Patent is hereby corrected as shown below:

IN THE SPECIFICATION:
At column 3, line 59, please replace "those killed in the art" with --those skilled in the art--.
At column 8, line 18, please replace "is given is given" with --is given--.

IN THE CLAIMS:
Claim 2, at column 12, line 51, replace "static drug" with --statin drug--.
Claim 21, at column 14, lines 19-20, replace "patients own blood" with --patient's own blood--.

Signed and Sealed this

Third Day of April, 2007

JON W. DUDAS
*Director of the United States Patent and Trademark Office*